(12) United States Patent
Auten et al.

(10) Patent No.: US 7,943,667 B2
(45) Date of Patent: May 17, 2011

(54) POTENTIATING THE EFFECT OF COMPOUND COMPRISING NITRIC OXIDE

(75) Inventors: Richard L. Auten, Chapel Hill, NC (US); Richard Whorton, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 12/675,822

(22) PCT Filed: Oct. 2, 2008

(86) PCT No.: PCT/US2008/011373
§ 371 (c)(1),
(2), (4) Date: Jun. 14, 2010

(87) PCT Pub. No.: WO2009/048521
PCT Pub. Date: Apr. 16, 2009

(65) Prior Publication Data
US 2010/0256237 A1      Oct. 7, 2010

Related U.S. Application Data

(60) Provisional application No. 60/960,719, filed on Oct. 11, 2007.

(51) Int. Cl.
*A61K 31/195* (2006.01)
*A61K 31/21* (2006.01)
*A61K 33/00* (2006.01)

(52) U.S. Cl. .......... 514/562; 514/509; 424/718
(58) Field of Classification Search .......... 514/562, 514/509; 424/718
See application file for complete search history.

(56) References Cited

U.S. PATENT DOCUMENTS 5,485,827 A      1/1996   Zapol et al.
2004/0224899 A1  11/2004  Gaston et al.

OTHER PUBLICATIONS

S. Singh et al., Nitric oxide, the biological mediator of the decade: fact or fiction?, European Respiratory Journal, 1997, pp. 699-707.

*Primary Examiner* — Raymond Henley, III
(74) *Attorney, Agent, or Firm* — Bacon & Thomas, PLLC

(57) ABSTRACT

Treatment of or prophylaxis against the occurrence of pulmonary disorders associated with hypoxemia and/or smooth muscle constriction or infection in the lungs comprises administration into the lung(s) as a gas composition comprising nitric oxide, e.g. ethyl nitrite or nitric oxide, and also administering into the lungs L-cysteine. The pulmonary disorder can be persistent pulmonary hypertension of the newborn to increase SpO2 and decrease systolic blood pressure. In another case administration is to a premature newborn to prophylax against the development of bronchopulmonary dysplasia.

3 Claims, No Drawings

POTENTIATING THE EFFECT OF COMPOUND COMPRISING NITRIC OXIDE

CROSS-REFERENCE RELATED APPLICATION

This application claims the benefit of U.S. Provisional Application No. 60/960,719, filed Oct. 11, 2007, the whole of which is incorporated herein by reference.

TECHNICAL FIELD

This invention relates to the treatment of respiratory, cardiac and blood disorders by delivery into the lungs of a composition comprising nitric oxide and composition comprising L-cysteine.

BACKGROUND OF THE INVENTION

Use of inhaled nitric oxide has been tested for a number of disease conditions and has been approved for the treatment of persistent pulmonary hypertension of the newborn. More recently, inhaled nitric oxide has been tested in clinical trials to test the hypothesis that inhaled nitric oxide could prevent the development of bronchopulmonary dysplasia in premature newborns.

Use of inhaled nitric oxide to treat pulmonary vasoconstriction and asthma is described in Zapol U.S. Pat. No. 5,823, 180. Bloch et al. U.S. Pat. No. 6,935,334 teaches administration of nitric oxide together with N-acetylcysteine functioning as an anti-oxidant to protect against destruction of nitric oxide. Pro-cysteine has the same function.

Stamler et al. U.S. Pat. No. 5,314,996 teaches administration into the lungs as a gas, of a compound with a nitric oxide group which does not form $NO_2/NO_x$, in the presence of oxygen or a reactive oxygen species (excludes nitric oxide), preferably ethyl nitrite (ENO), to treat pulmonary disorders associated with hypoxemia and/or smooth muscle constriction and cardiac and blood disorders. In cases, the treating agent is administered with intravenous or nebulized thiol, e.g. N-acetylcysteine, glutathione or cysteinylglycine to cause systemic release of nitric oxide from binding to cysteine of hemoglobin.

Stamler et al. U.S. Pat. No. 7,045,152 teaches treating pulmonary disorders in which the S-nitrosoglutathione (GSNO) pool or glutathione pool in the lung is depleted and where reactive oxygen species in the lung are increased, by delivering into the lung an agent causing repletion or increase in the GSNO pool or protection against toxicity and does so independently of reaction of oxygen (excludes administration of inhaled nitric oxide), e.g. ethyl nitrite, optionally with additional treatment of administration of intravenous or nebulized N-acetylcysteine as a GSNO pool repleting agent and/or to potentiate the effect of other GSNO repleting agent (ethyl nitrite).

SUMMARY OF THE INVENTION

This invention is supported by the discoveries (1) that molecules which donate free nitric oxide (.NO in radical form) and those which donate nitric oxide predominantly as nitrosonium ($^+$NO) achieve maximum intracellular S-nitrosothiol signal only in the presence of L-cysteine, i.e. that L-cysteine is required for maximum uptake of S-nitrosothiols from airway lining into lung; and (2) that L-cysteine acts as the, major carrier of S-nitrosothiol equivalents into lung cells.

The invention herein is directed to treatment of or prophylaxis against the occurrence of pulmonary disorders associated with hypoxemia and/or smooth muscle contraction or inflammation in the lung(s), by a method comprising administering into the lungs as a gas a therapeutically effective amount of composition comprising nitric oxide, that is nitric oxide or of compound which has NO group which is bound in the compound so that it does not form $NO_2$ or $NO_x$ (i.e., NO, $N_2O_3$, $N_2O_4$, $OONO^-$, OONO. and any products of their interaction or reaction with NO or $NO_2$) and administering into the lungs a therapeutically effective amount of L-cysteine (which forms S-nitroso-L-cysteine after the administration of the L-cysteine; the S-nitroso-L-cysteine is believed to be the actual therapeutic agent).

DETAILED DESCRIPTION

The pulmonary disorder can be, for example, pulmonary hypertension including persistent pulmonary hypertension of the newborn, acute respiratory distress syndrome (ARDS), asthma, cystic fibrosis or pneumonia.

In the case of prophylaxis against the occurrence of pulmonary disorders, a method herein is directed against development of bronchopulmonary dysplasia in premature newborn infants.

In the case of treatment of pulmonary disorders and prophylaxis against occurrence of pulmonary disorders, a compound comprising nitric oxide has a hypoxemic relieving and a smooth muscle constriction relieving effect.

The compounds comprising nitric oxide for treating pulmonary disorders and prophylaxis against the occurrence of pulmonary disorders, include, for example, nitric oxide and compounds having the formula $X-NO_y$ where X is an oxygen, sulfur, nitrogen or metal selected, for example, from the group consisting of iron, copper, ruthenium and cobalt atoms or an alkyl or alkenyl or alkylthio or alkenylthio group containing from 1 to 6 carbon atoms which is straight chain or branched, $CF_3$— and $CF_3S$—, and y is 1 or 2, provided that when x is oxygen, y is 2. Specific treating agents include, for example, nitric oxide (NO), ethyl nitrite (ENO) (which is used in examples herein), methyl nitrite, tert-butyl nitrite, isoamyl nitrite, trifluoronitrosomethane ($CF_3NO$), $CF_3SNO$, $CH_3SNO$, $CH_2$=CHSNO, $CH_2$=CHCH$_2$SNO, ONSCH$_2$—CH$_2$—CH$_2$SNO and $CH_3CH_2CH_2SNO$. Alkyl nitrites can be prepared as described in Landscheidt et al. U.S. Pat. No. 5,412,147. Nitric oxide in nitrogen is available commercially. Ethyl nitrite is available commercially, e.g., diluted in ethanol. $CF_3NO$ is a commercial product or can be made by treatment of $CF_3I$ with $NO^-$ as described in J. Phys. Chem. 100, 10641 (1996). Aliphatic thionitrites, i.e., compounds of the form RSNO where R describes an alkyl or alkenyl moiety, can be prepared by treatment of the corresponding thiol with a source of $NO^+$ including, but not limited to, one or more of the following: tert-butyl nitrite, ethyl nitrite, nitrosonium tetrafluoroborate ($NOBF_4$), nitrosonium perchlorate ($NOClO_4$), nitrosonium hydrogen sulfate ($NOHSO_4$), nitrosonium hydrogen phosphate ($NOH_2PO_4$), or HCl-acidified solutions of sodium nitrite.

We turn now to the administration of the compounds comprising nitric oxide. Those that are normally gases are readily administered diluted in nitrogen or other inert gas and can be administered in admixture with oxygen. Those that are not normally gases are converted to gas for administration and are administered diluted as in the case of the NO-containing compounds that are normally gases. The compounds should not have a boiling point such that the temperature required to maintain them as gases in diluted form would harm the lungs and preferably would not condense in the lungs.

Dilution, for example, to a concentration of 1 to 100 ppm is typically appropriate. For ENO and NO, dilution to 1-50 ppm is preferred.

The diluted gas is readily delivered into the lungs, using a ventilator which is a conventional device for administering gases into the lungs of a patient. A tube attached to the device passes the gas into the lungs at a rate and pressure consistent with maintaining a $Pa_{O2}$ of 90 mm Hg. Time periods of administration typically range from 1 minute to two or more days, and administration is carried out until symptoms abate. Administration can also be carried out using a face mask.

Ethyl nitrite is readily delivered using commercially prepared cylinders containing ethyl nitrite at 1000 ppm with the balance gas of nitrogen. These are prepared by Custom Gas Solutions, Durham NC, under license by N30 Pharma, which holds a patent on ethyl nitrite. Inhaled nitric oxide is delivered using a commercially FDA-approved delivery system, provided by INO Therapeutics (INOMax). In all cases, as presently determined, preferred nitric oxide providing compound is ethyl nitrite.

We turn now to amounts administered, i.e. dosage.

As indicated above, a therapeutically effective amount is administered. This is a hypoxemia relieving effective amount and smooth muscle constriction relieving effective amount for pulmonary disorders associated with smooth muscle constriction in lungs or inflammation in lungs resulting from injury or infection. A therapeutically effective amount for treating persistent pulmonary hypertension of the newborn is a hypoxemia relieving effective amount and a smooth muscle constriction effective relieving amount. For preventing development of bronchopulmonary dysplasia in premature newborns, doses of 5-10 ppm have shown some benefit.

These amounts are inherent in the administration protocol set forth above.

We turn now to the therapeutically effective amount of L-cysteine. The cysteine is preferably administered diluted in phosphate buffered saline pH 7.0 using a commercial disposable nebulizer in line with the inspiratory limb of the ventilator circuit, or affixed to a face mask for non-ventilated patients. The nebulizer delivers aerosol droplets at a geometric mean diameter of 1 micron, which is optimal for alveolar deposition. A target concentration for L-cysteine in the alveolar lining fluid is 10-50 micromolar. The dose of cysteine is inferred from the observation that cysteine concentrations in the alveolar lining fluid typically are ~10% of the amount of glutathione in the lining fluid. It is therefore assumed that the target cysteine concentration will be approximately 20 micromolar. Assuming that patients at high risk for defective NO signaling will also have both glutathione and cysteine depletion, an increase of 15 micromolar is targeted. Assuming that the epithelial lining fluid is about 1 ml/kg, and that only 5-10% of the nebulized droplets will deposit onto the epithelial lining fluid, it is calculated that about $3 \times 10^{-7}$ moles/kg of body weight is needed. With the molecular weight of L-cysteine=121 g/mole, this equates to 36 micrograms/kg of body weight, delivered in 50 microliters/kg of phosphate-buffered saline via nebulizer. Thus, to achieve the target concentration of 10-50 micromolar in the alveolar lining fluid, we would administer nebulized L-cysteine in amounts equal to 18-90 microgram/kg of body weight.

As a result of the presence of cysteine, the composition comprising nitric oxide is more potent (allowing, for example, reduction of 80% in amount administered, e.g. reduction of 80% ethyl nitrite administered) and acts faster (e.g., providing benefit 500% faster, e.g. in one minute rather than 5 minutes.

Support for conception and background of the invention is found in Granillo, O.M., et al., AM. J. Physiol. Lung Cell Mol. Physiol 295: 38-43 (first published Apr. 25, 2008.), the whole of which is incorporated herein by reference.

Support for and illustration of the invention is found in the following Background Examples and Working Examples.

BACKGROUND EXAMPLE 1

The following shows progression on the way to conception:

It was shown in a kidney cell line that transportation of extracellular S-nitrosothiols in the form of S-nitroso-L-cysteine through the L-type amnio acid transporter (LAT1) is necessary to achieve maximum intracellular S-nitrosothiol accumulation. It was also shown that eliminating the L-type amino acid transporter or blockade of the transporter severely limited the ability of extracellular S-nitroso-L-cysteine to gain entry into the kidney cell line. Based on these results, we conceived that abnormalities of the L-type amino acid transporter or its uptake of L-cysteine could explain the apparent lack of efficiency of inhaled nitric oxide in subsets of premature babies treated for prevention of occurrence of bronchopulmonary dysplasia. The results for kidney cell line were then obtained for umbilical endothelial cells. This reinforced our conception. We then performed exposures of rat pulmonary alveolar epithelial cells to a variety of S-nitrosothiol and nitric oxide donors and tested whether or not S-nitrosothiol and nitric oxide uptake required transnitrosylation of L-cysteine and uptake through L-type amino acid transport. In particular we conducted experiments using rat alveolar epithelial cells. We found that molecules which donated free nitric oxide (.NO in radical form) and those which donated nitric oxide predominantly as nitrosonium ($^+$NO) achieved the maximum intracellular S-nitrosothiol signal only in the presence of L-cysteine. We found that when we blocked the L-type amino acid transporter, this effect was inhibited. We also tested the dipeptide transporter, PEPT2. We found that a dipeptide that should be taken up through that transporter, namely L-cysteinyl-glycine, in lung cells was in fact taken up, but that when we chemically modified L-cysteinyl-glycine to form S-nitroso-L-cysteinyl-glycine, we could not achieve high levels of S-nitrosothiol signal in lung cells with this modified compound. When we added L-cysteine to the mixture, the high levels of S-nitrosothiol uptake in lung cells were restored, and this restoration was blocked when we blocked function of L-type amino acid transporter by competition or inhibition. The concentrations of L-cysteine we used to achieve this result are comparable to levels we might expect to find in lung lining fluid of humans.

We conducted additional studies to determine if an alternate transporter, namely PEPT2, could account for some of the S-nitrosothiol uptake in lung cells. We found that PEPT2 is present in cultured lung cells, and that it can take up other dipeptides like radio labeled glycyl-sarcosine. However, we found that treatment with S—NO-Cys-Gly did not significantly increase accumulation of S-nitrosothiol or free nitric oxide in lung cells, unless we also added L-cysteine. This confirmed the importance of L-cysteine as the carrier which is necessary to achieve high levels of S-nitrosothiols in lung cells. We confirmed these finding in freshly isolated lung cells as well.

As a result of the above, we conceived that premature babies at risk to develop bronchopulmonary dysplasia would benefit by co-treatment of inhaled nitric oxide with aerosolized L-cysteine, by reduction of lung injury and improvement of clinical outcomes.

BACKGROUND EXAMPLE 2

In this example ENO means ethyl nitrite and DAF-FM means (4-amino-5-methylamino-2',7'-difluorofluorescein) diacetate.

Rat alveolar (L2) cells were located with DAF-FM (converted intracellularly to DAF; $NO^+ + DAF \rightarrow$ fluorescense), then incubated with ENO 10 mM+L-Cys 0.5 mM, L-Leu 10 mM (competitor for L-Cys entry via LAT1), or both L-Cys+L-Leu. DAF signal was measured at 5, 10, and 24 min. In parallel studies, S—NO was measured in L2 cell lysates after co-incubation with ENO 0.2 mM±L-Cys 0.5 mM±L-Leu 10 mM by ozone chemiluminescense (normalized to protein). LAT1 protein was detected by western and immunocytochemistry in 8d air or 95% $O_2$—exposed rat lung.

Results obtained are set forth below.

Cys augmented ENO induced intracellular NO signal (DAF) by 24 minutes, but significantly less (N=5/group p<0.05) with Leu (competitor for LAT1). ENO+Leu induced high $NO^+$ at all time points. Cys treatment augmented ENO induced SNO accumulation (N=2/group). Leu treatment did not augment ENO induced SNO accumulation. Lung LAT1 expression was not augmented by $\uparrow O_2$ and was found chiefly lining alveolar epithelium. Our conclusion from the above is: ENO increased intracellular $NO^+$ and SNO via LAT1 dependent paths, probably including diffusion and other transporters suggesting that LAT1 may partially regulate inhaled ENO-induced S-nitrosylation in lung.

BACKGROUND EXAMPLE 3

We carried out experiments showing that addition of L-Cys to NO donors increased SNO/NO accumulation that was inhibited by co-incubation with LAT competitors in rat alveolar pulmonary epithelial cells (L2 and Type II). These are described in Granilla, O. M., AM. J. Physiol Lung Cell Mol. Physiol 295: L38-L43 (first published Apr. 25, 2008).

BACKGROUND EXAMPLE 4

Cells were plated onto rat-tail collagen coated plastic inserts in a transwell system. When cells were firmly adherent and intact in appearance by microscopy, usually 24 h after plating, cell inserts were incubated in DAF-FM diacetate for one hour, then rinsed in Hepes-buffered Hank's balanced salt solution without amino acids. Buffer was removed from the upper chamber of the transwell and replaced with phosphate-buffered saline containing 0.2 mM glutathione in order to mimic the glutathione levels found in human alveolar lining fluid. This buffer was added alone, or containing D-cysteine, L-cysteine, L-cysteine+L-leucine (competitor), or L-cysteine+BCH (competitor); BCH is 2-aminobicyclo-(2,2,1)-heptane-2-carboxylic acid. The volume added was a few microliters sufficient to produce a layer of buffer ~2 micron in thickness, in an effort to model the alveolar lining fluid thickness in the mammalian lung. Cell inserts were incubated at air liquid interface for 30 minutes, then exposed to NO or ENO gas 10 ppm for 4 hours. Inserts were then placed into a fluorescent microplate reader to detect the intracellular NO signal.

Incubation with D-cysteine, as expected, had no effect on NO signal produced by ENO or NO gas, in sharp contrast with the effect of L-cysteine. Treatment with LAT competitors L-leucine and BCH completely abolished the L-cysteine augmentation of NO signal. These studies show that maximum intracellular signal from NO or ENO gas requires L-cysteine to achieve cell entry, and that this entry takes place via LAT, since LAT competitors blocked signal, and D-cysteine treatment (LAT is stereoselective) did not augment the signal. We concluded that co-treatment of ENO or NO with inhaled L-cysteine will increase intracellular NO bioavailability and will likely improve its potency and potentially its efficacy.

BACKGROUND EXAMPLES 5

Rat L2 (alveolar) cells were used at passage 30. 1° alveolar T1/T2 cells were isolated from adult rat lungs with antibody-coated magnetic beads, and identified by immunocytochemistry (T1: $T1^\alpha$, aquaporin-5; T2: pro-SP-C). Alveolar macrophages were obtained by lavage. Cells were plated onto collagen-coated transwells, grown submerged×2d, then incubated with DAF-FM to detect NO. Apical medium was replaced by buffer+glutathione 0.2 mM,±D-or L-Cys 50 µM±LAT competitors L-Leu or BCH, 10 mM×1 h then exposed to air or NO gas 10 ppm×4 h. Fluorescence was read in 4-8 wells/condition. LAT-1 expression was measured/RT-PCR in air or 95% $O_2$-exposed newborn rat lung (day 2, 3, 4, 8).

All cell types expressed LAT-1. Incubation with L-but not D-Cys increased NO signal in all cell types (mean of 4-8 wells/group±SEM, normalized to L-Cys, p<0.05v.L-Cys). This was blocked by competitors Leu and BCH. Results in alveolar macrophages were parallel but at lower magnitude than in L2, T1, or T2 cells. 95% $O_2$ impaired lung LAT-1 expression at 2-4 d, but not 8 d. Our conclusions are that NO gas at air-liquid interface achieves maximum NO levels in alveolar epithelium and alveolar macrophages through LAT. We speculate that defects in LAT expression may impair iNO pharmacologic effects that may be overcome if L-Cys is supplemented. Furthermore, L-Cys treatment may augment iNO pharmacologic effects by increasing NO uptake if LAT uptake is intact.

BACKGROUND EXAMPLE 6

Newborn piglet was anesthetized and a thoracotomy was performed after placing arterial and venous monitoring catheters. A catheter was placed in the pulmonary artery and flow sensors around the pulmonary artery were placed. The lungs of the piglet were lavaged with normal saline to induce a lung injury that resulted in elevated pulmonary artery pressures consistent with pulmonary hypertension. Inhaled nitric oxide was administered at 10 ppm which reduced the peak pulmonary pressure from 56 Torr to 45 Torr Combining the administration of nebulized L-cysteine with inhaled nitric oxide further reduced the pulmonary artery pressure to 40 Torr, demonstrating augmentation of the NO effects.

WORKING EXAMPLE I

A newborn is delivered at 41 weeks gestational age through thick meconium following a labor requiring augmentation with oxytocin. He is immediately noted at birth to experience respiratory distress and cyanosis. His pulse oximetry shows a SpO2=82% which only rises to 88% with the administration of 100% oxygen by oxygen tent. A chest radiograph shows relatively clear lung fields and a slightly enlarged heart. His respiratory distress worsens requiring mechanical ventilation. An echocardiogram is obtained which demonstrates right ventricular dysfunction, tricuspid regurgitation, ventricular septal bowing into the left ventricle, and a calculated suprasystemic right ventricular systolic pressure. The patient is treated with 36 micrograms/kg of L-cysteine by nebulizer attached to the inspiratory limb of the ventilator circuit, followed by initiation of inhaled ethyl nitrite or inhaled nitric oxide at 1-50 ppm. The patient SpO2 rises immediately from 88% to 100%, and systolic blood pressure improves. This example represents treatment of persistent pulmonary hypertension of the newborn.

WORKING EXAMPLE II

The patient is born at 25 weeks estimated gestational age following preterm prolonged spontaneous rupture of amniotic membranes. The patient requires immediate endotracheal intubation at birth as well as mechanical ventilation. The patient receives the usual neonatal intensive care including exogenous surfactant administration, indomethacin prophylaxis for prevention of intraventricular hemorrhage, and intravenous antibiotics. Because the patient is at high risk to develop bronchopulmonary dysplasia, the patient is treated each day with a single dose of 36 micrograms/kg of L-cysteine and continuous ethyl nitrite at 1-10 ppm for a total of 14 days. (This is done via face mask unless the patient should be extubated, in which case the inhaled ethyl nitrite is delivered via nasal cannula and the L-cysteine is administered once a day via nebulizer) Within five days, the patient is weaned from mechanical ventilation and extubated to nasal continuous positive airway pressure, continuing to receive inhaled nitric oxide 1-10 ppm, and daily L-cysteine at 36 micrograms/kg. At age 14 days, the continuous positive airway pressure is discontinued. By age 11 weeks, a physiological oxygen challenge test is performed, demonstrating no requirement for supplemental oxygen at 36 weeks post conceptual age, and therefore no evidence of bronchopulmonary dysplasia. By age 14 weeks the patient is discharged home, without any diagnosed complications of extreme prematurity. This example represents prevention of development of bronchopulmonary dysphasia in a premature newborn infant.

VARIATIONS

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A method of treatment for a patient having pulmonary hypertension or a newborn at risk for development of broncopulmonary dyplasia comprising administering to the patient or newborn a therapeutically effective amount of nebulized L-cysteine and a therapeutically effective amount of agent selected from the group consisting of nitric oxide and ethyl nitrite.

2. The method of claim 1 persistent pulmonary hypertension of the newborn is treated and the treatment effects increase in SpO2 and decrease in systolic blood pressure.

3. The method of claim 1 where treatment is of a premature newborn at risk for development of bronchopulmonary dysplasia and is to prevent development of broncopulmonary dyplasia.

* * * * *

UNITED STATES PATENT AND TRADEMARK OFFICE
CERTIFICATE OF CORRECTION

| | |
|---|---|
| PATENT NO. | : 7,943,667 B2 |
| APPLICATION NO. | : 12/675822 |
| DATED | : May 17, 2011 |
| INVENTOR(S) | : Richard L. Auten and Richard Whorton |

It is certified that error appears in the above-identified patent and that said Letters Patent is hereby corrected as shown below:

Column 8, line 23, add --where-- between "1" and "persistent".

Signed and Sealed this
Fourteenth Day of June, 2011

David J. Kappos
*Director of the United States Patent and Trademark Office*